United States Patent
Axen et al.

(10) Patent No.: US 7,988,858 B2
(45) Date of Patent: Aug. 2, 2011

(54) METHOD FOR GENERATING METAL CHELATING AFFINITY LIGANDS

(75) Inventors: Andreas Axen, Uppsala (SE); Jean-Luc Maloisel, Uppsala (SE); John Clachan, Uppsala (SE); Helena Lindgren, Uppsala (SE); Anne Catharina Bergh, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 472 days.

(21) Appl. No.: 12/297,231

(22) PCT Filed: May 23, 2007

(86) PCT No.: PCT/EP2007/004583
§ 371 (c)(1),
(2), (4) Date: Oct. 15, 2008

(87) PCT Pub. No.: WO2007/137752
PCT Pub. Date: Dec. 6, 2007

(65) Prior Publication Data
US 2009/0200239 A1    Aug. 13, 2009

(30) Foreign Application Priority Data

May 26, 2006 (GB) .................................. 0610479.8

(51) Int. Cl.
*B01D 15/08* (2006.01)
(52) U.S. Cl. ............ 210/635; 210/656; 210/198.2; 210/502.1; 502/401; 502/439
(58) Field of Classification Search .................. 210/635, 210/656, 659, 679, 198.2, 502.1; 502/401, 502/402, 439
See application file for complete search history.

(56) References Cited

U.S. PATENT DOCUMENTS

| | | | |
|---|---|---|---|
| 4,551,271 A | 11/1985 | Hochuli | |
| 4,877,830 A | 10/1989 | Dobeli et al. | |
| 5,310,663 A | 5/1994 | Dobeli et al. | |
| 6,623,655 B1 * | 9/2003 | Kappel et al. | 252/1 |
| 7,005,071 B2 * | 2/2006 | Andersson et al. | 210/635 |
| 7,067,059 B2 * | 6/2006 | Maloisel et al. | 210/635 |
| 7,320,754 B2 * | 1/2008 | Carlsson et al. | 210/635 |
| 2007/0027303 A1 * | 2/2007 | Rybka et al. | 530/317 |

FOREIGN PATENT DOCUMENTS

| | | |
|---|---|---|
| GB | 707709 | 4/1954 |
| WO | WO 88/07414 | 10/1988 |
| WO | WO 01/81365 | 11/2001 |
| WO | WO 03/087047 | 10/2003 |
| WO | WO 2004/076475 | 9/2004 |
| WO | WO 2004/078311 | 9/2004 |

* cited by examiner

OTHER PUBLICATIONS

Hjerten, S., "The Preparation of Agarose Spheres for Chromatography of Molecules and Particles" Biochimica et Biophysica Acta, 79 (1964) 393-398.

*Primary Examiner* — Ernest G Therkorn
(74) *Attorney, Agent, or Firm* — Yonggang Ji

(57) ABSTRACT

The present invention relates to a method for generating at least one polydentate metal chelating affinity ligand, which method comprises the steps of
(a) providing at least one scaffold defined by the general formula (I): $H_2N-(X_1)_n-S-S-(X_2)_m-CH_2-NH_2$ wherein $X_1$ and $X_2$ irrespective of each other are carbon atoms or heteroatoms, and n and m irrespective of each other are integers of 1 to 5;
(b) providing at least one polydentate metal chelating affinity ligand arm, optionally in a form wherein the metal chelating functionalities of at least one arm are protected, on each scaffold by derivatisation of the nucleophilic $NH_2$ groups of the scaffold;
(c) reducing the disulfide bond of the derivatised scaffold; and, if required
(d) deprotecting the functionalities of the ligand arm(s) provided in step (b). In the most preferred embodiment, the reduction of the disulfide bond and the deprotection step is performed essentially simultaneously.

16 Claims, 4 Drawing Sheets

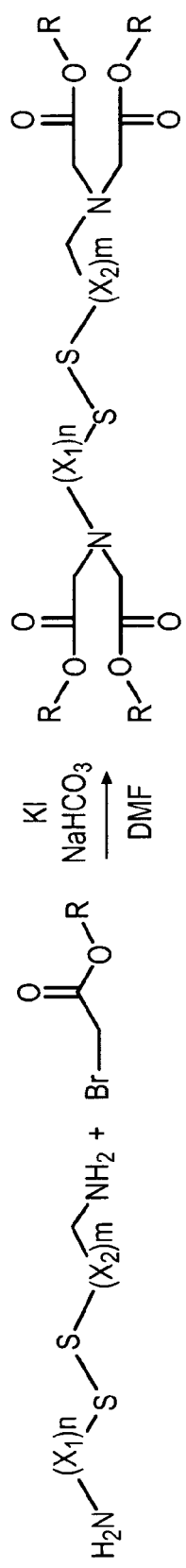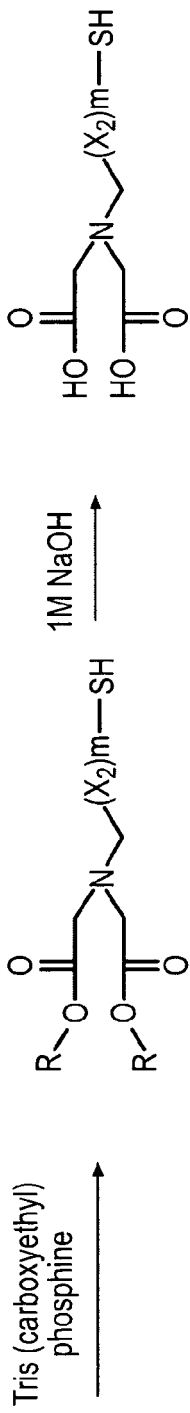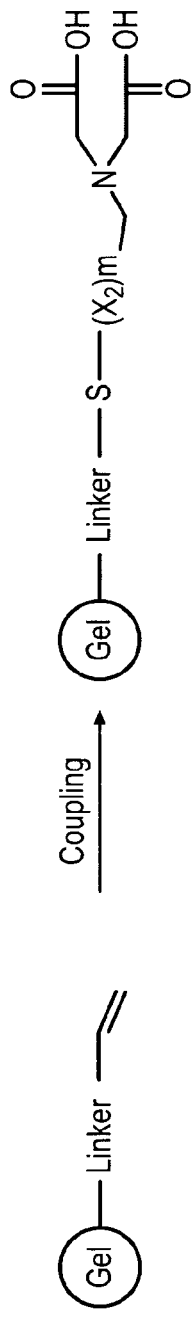
Fig. 1a
Fig. 1b

METHOD FOR GENERATING METAL CHELATING AFFINITY LIGANDS

CROSS-REFERENCE TO RELATED APPLICATIONS

This application is a filing under 35 U.S.C. §371 and claims priority to international patent application number PCT/EP2007/004583 filed May 23, 2007, published on Dec. 6, 2007, as WO 2007/137752, which claims priority to patent application number 0610479.8 filed in Great Britain on May 26, 2006.

FIELD OF THE INVENTION

The present invention relates to a method of generating polydentate metal chelating affinity ligands. The invention also encompasses a method of generating a separation medium comprising such ligands, as well as such ligands and such a medium.

BACKGROUND OF THE INVENTION

In any chemical or bioprocessing industry, the need to separate and purify a product from a complex mixture is a necessary and important step in the production process. Today, there exists a wide market of methods in which industry can accomplish these goals, one of which is chromatography. Chromatography is well suited to a variety of uses in the field of biotechnology since it can separate complex mixtures with great precision; in particular, chromatography is very well suited to the separation of more delicate or sensitive products, such as proteins, since the conditions under which it is performed are not typically severe.

One chromatography method, which is an especially sensitive separation technique and is also applicable to most types of proteins, is metal chelate affinity chromatography (MCAC), also known as immobilised metal ion adsorption chromatography (IMAC). This technique is commonly used in purification schemes together with another chromatographic step, such as ion exchange chromatography (IEX) and/or hydrophobic interaction chromatography (HIC).

More specifically, IMAC utilises matrices that comprise a group capable of forming a chelate with a transition metal ion, which chelate in turn is used as the ligand in chromatography to adsorb a compound from a liquid. The binding strength in IMAC is affected predominately by the species of metal ion, the pH of the buffer and the nature of the ligand used. Since the metal ions are strongly bound to the matrix, the adsorbed protein can be eluted either by lowering the pH or by competitive elution (for example, with imidazole).

In general, IMAC is useful for the separation of proteins or other molecules that present an affinity for the transition metal ion of the matrix. For example, proteins will bind to the matrix upon the presence of accessible histidine, cysteine and tryptophan residues, which all exhibit an affinity for the chelated metal.

With the advent of molecular biological techniques, proteins are now easily tailored or tagged with one or more histidine residues in order to increase their affinity to metal chelated ligands, and accordingly, metal chelate chromatography has more recently assumed a more important role in the purification of proteins. (e.g. U.S. Pat. No. 5,310,663, Döbeli et al, assigned to Hoffman-La Roche Inc.). Simple chelators have been suggested as ligands for IMAC, such as iminodiacetic acid (IDA). IDA, coupled to agarose supports and subsequently charged with various metals, such as $Cu^{2+}$, $Zn^{2+}$ and $Ni^{2+}$, has been used for the capture of proteins and peptides and is also available as a commercial resin. More specifically, U.S. Pat. No. 4,551,271 (Hochuli, assigned to Hoffmann-La Roche Inc.) discloses a metal chelate resin which comprises IDA ligands, in the purification of interferon. The resin can be defined by the following formula:

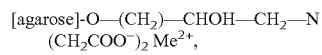

wherein Me is Ni or Cu.

The best results are obtained with this resin if the interferon has already been partially purified. The resin can according to the specification be prepared in a known manner by treating agarose with epichlorohydrin or epibromohydrin, reacting the resulting epoxide with iminoacetic acid disodium salt and converting the product into the copper or zinc salt by washing with a copper (II) or zinc solution.

More recently, EP 87109892.7 (F. Hoffmann-La Roche AG) and its equivalent U.S. Pat. No. 4,877,830 (Dobeli et al, assigned to Hoffmann-La Roche Inc.) disclosed a tetradentate chelator known as nitrilotriacetic acid (NTA) for use with metals that have six coordination sites. More specifically, the matrices can be described by the general formula:

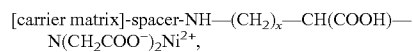

wherein x=2-4.

The disclosed matrix is prepared by reacting an amino acid compound of the formula R—HN—$(CH_2)_x$—CH$(NH_2)$—COOH, wherein R is an amino protecting group and x is 2, 3 or 4, with bromoacetic acid in alkaline medium and subsequently, after an intermediate purification step, cleaving off the protecting group and reacting this group with an activated matrix. Accordingly, the method of preparation involves separate steps for alkylating and deprotecting the amino acid, which steps renders the method time-consuming and hence costly. In addition, the alkylation chemistry is less efficient, and after deprotection, the product is not well defined following neutralisation and cleavage. Subsequently, the material is coupled to a solid support that carries carboxyl functionalities by forming an amide bond. However, several problems may be encountered in using this procedure as the media obtained comprises both the desired immobilised chelating ligand as well as some unreacted carboxylic groups and is thus heterogeneous in nature. Furthermore, mono-N-protected amino acid compounds are expensive starting materials, rendering the overall method even more costly.

WO 01/81365 (Sigma-Aldrich Co.) discloses a metal chelating composition that according to the specification is capable of forming relatively stable chelates with metal ions that exhibits an improved selectivity for polyhistidine tagged proteins. According to WO 01/81365, the linkage between the chelator and the resin is an important parameter for the selectivity, and the linkage is a neutral ether, a thioether, a selenoether or an amide. The disclosed compositions are coupled to an insoluble carrier, such as SEPHAROSE™ according to given examples. The chromatographic media is produced in two different ways; either by a solid phase reaction directly on to the pre-activated solid support eventually used in the chromatographic media, or by a separate in-solution synthesis of the intermediate product N,N,N',N'-tetrakis(carboxymethyl)-L-cystine that is eventually coupled to the solid support.

The solid phase synthesis is carried out by adding L-cysteine to a previously epichlorohydrine activated SEPHAROSE™ gel under alkaline conditions for a prolonged reaction time (18 h), followed by washings. Thereafter bromoacetic acid is added under basic conditions and a prolonged reaction time (72 h), again followed by washings, and any remaining free amino groups present on the gel capped with acetic acid anhydride. Solid phase synthesis in this way offers poor control of the reaction and potential side reactions, and thereby yields a less homogeneous product.

The alternative route, relying on in-solution phase synthesis of an intermediate product starts with addition of a large excess (40 times) of glyoxylic acid to L-cystine in an alkaline borate buffer. The intermediate product, following pH manipulation and conductivity adjustment of the reaction mixture, purified with ion exchange chromatography to give N,N,N',N'-tetrakis(carboxymethyl)-L-cystine.

Before coupling to a solid support the N,N,N',N'-tetrakis (carboxymethyl)-L-cystine has to be reduced to N,N-bis(carboxymethyl)-L-cysteine using tris(carboxyethyl)phosphine under alkaline conditions. This material can finally be used for coupling to a pre-activated solid support forming the chromatographic media. This synthetic method is elaborate and depends on a large excess of reagents to form the desired product that is eventually purified under specific chromatographic conditions, followed by reduction as an additional synthetic step, and is thereby less suited for use in large-scale production.

WO 2004/076475 (Andersson et al, Assigned to Amersham Bio-Sciences AB) discloses a method of generating polydentate metal chelating affinity ligands which can subsequently be coupled to a base matrix. The method involves providing a cyclic scaffold comprising a carbonyl, an adjacent sulfphur and a nucleophile; providing a polydentate metal chelating affinity ligand arm on each scaffold by derivatisation of the nucleophile, ring-opening of the cyclic scaffold by addition of reagent that adds more metal chelating affinity ligand arm(s) to the scaffold; and, if required, deprotecting the functionalities of the ligand arm(s). The preferred ligands (which comprise NTA), when coupled to a base matrix, are useful in the purification of his-tagged proteins.

GB707709 discloses the synthesis of pantethein from cysteamine. The compound pantethein does not possess any metal chelating properties.

One key factor in the use of any IMAC ligand in separation media is that of metal binding capacity. The ligand must clearly be able to form a chelate with the transition metal ion of choice for the particular chromatographic separation. The binding capacity of the ligand for the metal ion will influence the conditions required for eluting the adsorbed substance, such as a protein, from the media (for example the pH or concentration of competitor eluant required). Another important factor, which is related to binding capacity, is that of metal leakage from the separation media. Clearly there is a desire to minimise metal leakage from the separation media as metals may be toxic or have adverse effects on the final product of the chromatographic separation. This is particularly true in the field of protein separations where metals may have inhibitory effects on protein function.

Separation media based upon known IMAC ligands vary in the degree to which they chelate or bind metals and also in the extent to which such metals leach from the media on elution with acidic or competitive eluants, such as imidazole.

Accordingly, there is still a need of improved methods for synthesis of IMAC ligands as well as of methods for the immobilisation thereof to a base matrix.

SUMMARY OF THE INVENTION

Thus, one object of the present invention is an improved method of generating polydentate metal chelating affinity ligands for subsequent coupling to a base matrix, which method utilises cost-effective and easily available starting materials and reagents. This can be achieved as defined in claim 1.

Another object of the present invention is to enable a careful selection of the ligands that are immobilised onto a base matrix for use in IMAC. This can be achieved by a method of generating a separation medium comprising polydentate metal chelating affinity ligands coupled to a base matrix, wherein the coupling chemistry is well defined and easy to control.

A further object of the invention is to provide such a method, which results in a homogenous product.

Yet a further object of the invention is to provide a method as discussed above, which also allows introducing two or more functionalities, which functionalities may be of the same kind or different.

Another object of the present invention is to provide ligands for immobilised metal affinity chromatography, which ligands present an improved handle for coupling to a base matrix and hence an improved coupling efficiency as compared to prior art ligands.

An additional object of the present invention is to provide a chromatographic medium, which in use for immobilised metal affinity chromatography has a high metal binding capacity and yields a low leakage of metal ions on elution. The objects of the invention can be achieved by one or more of the appended claims. Further objects, advantages and embodiments of the present invention will appear from the detailed description that follows.

BRIEF DESCRIPTION OF THE DRAWINGS

FIGS. 1 (*a*) and 1 (*b*) provide a schematic illustration of the general route to produce a separation medium that comprises polydentate metal chelating affinity chromatography ligands according to the invention.

FIG. 3 (*b*) shows the purification of the same protein from the same extract using Ni SEPHAROSE™ HP separation media (available from GE Healthcare Bio-Sciences AB, Uppsala, Sweden). In both FIGS. 3 (*a*) and (*b*), the imidazole gradient and the elution profile at 280 nm are shown.

DEFINITIONS

Figure 2A:
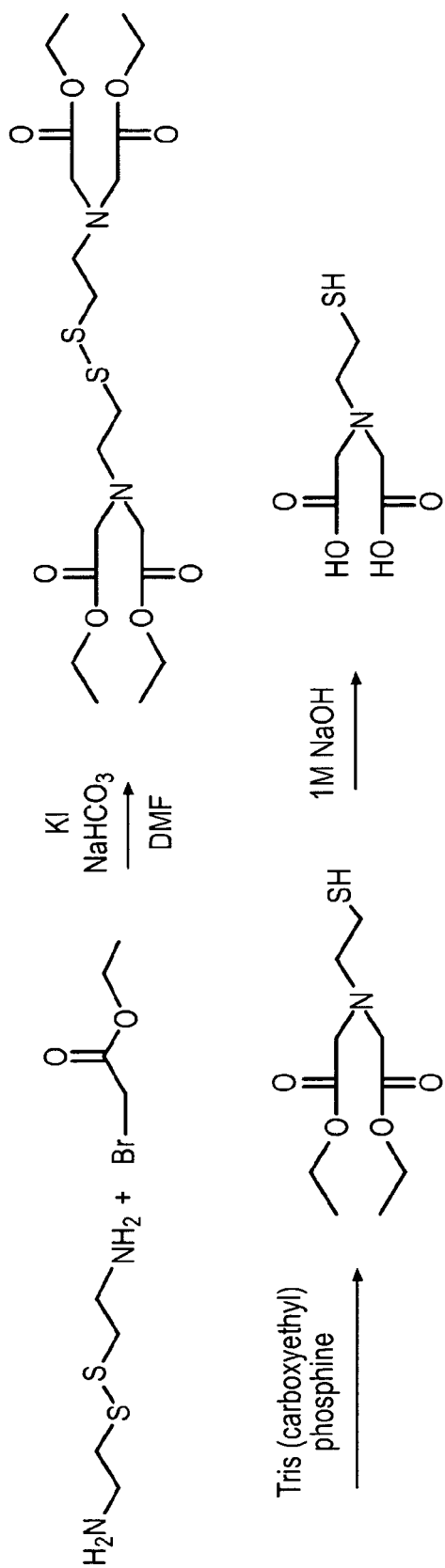
FIGS. 2 (*a*) and 2 (*b*) are a schematic illustration of a route to produce a separation medium that comprises polydentate metal chelating affinity chromatography ligands using a cystamine scaffold, in accordance with the invention.

The term "separation medium" is used herein for a material useful e.g. as packing for a chromatography column, and more specifically consists of one or more ligands coupled to a base matrix. Thus, the base matrix acts as a carrier, while the ligands provide functionalities that interact with target substances in chromatography.

The term "spacer" is used for a chemical entity that distances a ligand from the base matrix.

The term "ligand" means herein a chemical entity capable of binding target substances. Such target substances may be either a compound, which it is desired to isolate or remove by chromatography, or alternatively an analytical target substance. Preferably, the substance is a protein or peptide.

The term "polydentate metal chelating" ligands refers to ligands with two or more donor atoms that can coordinate to, i.e. chelate, a metal simultaneously. Thus, a polydentate ligand has two or more donor atoms and occupies two or more sites in a coordination sphere.

Thus, the term "metal chelating functionalities" refers to the groups that provide donor atoms. Usually, the functionalities are distanced from each other and hence the term "ligand arm" is used for each functionality. The term "gel" is used for a separation matrix, which is in the form of a gel.

DETAILED DESCRIPTION OF THE INVENTION

Thus, in a first aspect, the present invention relates to a method for generating at least one polydentate metal chelating affinity ligand, the method comprising the steps of;
(a) providing at least one scaffold defined by the general formula (I)

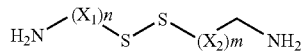

wherein $X_1$ and $X_2$ irrespective of each other are carbon atoms or heteroatoms, and n and m irrespective of each other are integers of 1 to 5;
(b) providing at least one polydentate metal chelating affinity ligand arm, optionally in a form wherein the metal chelating functionalities of at least one said ligand arm are protected, on each said scaffold by derivatisation of the nucleophilic $NH_2$ groups of the scaffold;
(c) reducing the disulfide bond of the derivatised scaffold; and, if required
(d) deprotecting the functionalities of the ligand arm(s) provided in step (b).

The scaffold of step (a) can be provided as a solid or, preferably, in a solvent. In the most advantageous embodiment, in formula (I), $X_1$ and $X_2$ are carbon atoms. In alternative embodiments, one or more of $X_1$ and $X_2$ are heteroatoms, i.e. selected from the group comprised of oxygen, sulphur and/or silica, provided that the heteroatom does not interfere in the subsequent use of the ligands.

As specified above, n can be any integer of 1 to 5 (i.e. 1, 2, 3, 4 or 5). Furthermore, irrespective of the value of n, m can be any integer of 1 to 5, i.e. 1, 2, 3, 4 or 5. As appears from the method steps, the value of m will decide the number of atoms between the ligand arms and its attachment point to a base matrix when it is developed into a separation medium.

In a preferred embodiment, in formula (I), n is 2 and m is 1 and the scaffold is cystamine (also known as 2,2'-dithiobisethanamine; 2,2'-dithiobis(ethyl-amine); and β,β'-diaminodiethyl disulfide). Cystamine dihydrochloride is commercially available from a number of suppliers (cf. CAS number 56-17-7).

In step (b), the derivatisation is performed by adding a suitable derivatisation agent comprised of a first part, which is electrophilic and hence capable of reacting with $NH_2$ of Formula (I), and a second part, which comprises a metal chelating functionality.

The first part of the derivatisation agent, i.e. the electrophilic part, can be illustrated by C=C; C—Y, wherein Y represents for example a halogen, such as Br, I, Cl, or a mesylate, or a tosylate group; or an acid or an activated acid such as WC=O, wherein W is for example formed from N-hydrosuccinimide, pentafluorophenol, para-nitrophenol or isopropyl chloroformate.

In an advantageous embodiment, the derivatisation is provided by adding two derivatisation agents, each one of which comprises different or identical metal chelating functionalities, herein denoted $L_1$ and $L_2$. In this embodiment, the electrophilic parts of the agents are preferably of the same nature in order to facilitate the derivatisation. In an alternative embodiment, more than two different or identical metal chelating functionalities are introduced by derivatisation of $NH_2$, preferably by use of two or more different steps, as is understood by the skilled person in this field. Accordingly, multiple functionalities are easily provided in the same, polydentate metal chelating affinity ligand.

The derivatisation agent(s) used in the present method can either comprise the metal chelating functionality in protected form, wherein the donor atoms are unavailable for reaction during the derivatisation of the scaffold, or in non-protected form. In the embodiment where the functionality is protected, said protecting group should be easy to remove in a subsequent step. Accordingly, the protecting group is either acid labile, such as an alkyl group, or base labile, such as a tertiary-butyl group. In one embodiment, the protecting group is a $CH_2CH_3$ group. Various metal chelating functionalities are known in this field, and can in principle be any electron-donating group. More specifically, the metal chelating functionalities used in the present method are selected from the group that consists of aromates, heterocyclic derivatives, such as pyridine, thiophene, furan and imidazole, acids, esters, ketones, amides, sulphones, sulphonamides, nitrile, carbon-carbon double and triple bonds.

In an illustrative embodiment, the derivatisation agent is an halogenated carboxylic acid ester, such as an halogenated carboxylic acid alkyl ester. Methods for reacting an $NH_2$ group with a group carrying an halogen or another leaving group are well known in this field and are conveniently performed at ambient temperature in a solvent such as N,N-dimethylformamide (DMF). In one embodiment, in order to provide two metal chelating affinity ligand arms on each scaffold by the derivatisation, the derivatisation agent is used in a molar ratio of 2:1 to the scaffold. The skilled person can easily monitor the reaction and confirm the derivatisation obtained by a conventional method such as LC-MS. Thus, the present invention provides a less complex synthetic route to polydentate metal chelating affinity ligands than WO 01/81365. Due to the advantageous chemistry, the present method also results in a more homogenous product which can be obtained using starting materials which are readily available at a reasonable cost. Thus, as indicated above, in the embodiment where the metal chelating functionalities $L_1$ and $L_2$ were protected during the derivatisation step, a step of deprotection is preferably performed. In one embodiment, said deprotection is performed as a separate step that follows step (c), and can be achieved by adding a base or an acid, as indicated above. The chemistry useful for protection/deprotection of functionalities is well-known in this field, and the skilled person in the art can easily perform such steps.

In an especially advantageous embodiment of the present method, the deprotection is performed in the same step as disulfide bond reduction (i.e. step (c)). Accordingly, the great advantage of this embodiment is that polydentate metal chelating affinity ligands can be generated using a two step procedure. Consequently, this embodiment provides a less complex method than many of the prior art methods for the synthesis of polydentate metal chelating affinity ligands. In one embodiment, wherein the derivatisation agent comprises a base labile group, this step is provided by addition of sodium hydroxide. The hydrolysis is advantageously performed at ambient temperature for e.g. 1-2 hours. In fact, the present inventors have also shown that even though all the starting material can be converted within 90 minutes, an additional 48 hours does not give rise to any side products. Accordingly, the hydrolysis according to the invention results in a stable, homogenous and well-defined product.

In an alternative embodiment, wherein the derivatisation agent comprises an acid labile group, step (c) is provided by addition of an acid, such as HCl.

In a specific embodiment, in the present method, steps (a) and (b) have been performed earlier to provide a ready-derivatised scaffold. Accordingly, the present invention also encompasses a method, wherein the carboxymethylation of the scaffold has been performed earlier.

In an advantageous embodiment, the product so obtained is coupled via its sulphur to a base matrix in order to produce a separation medium. Such a separation medium is useful for isolation of target substances, for analytical purposes etc. The base matrix used in the present method can be of any material suitable for the intended use.

Thus, in the case where the separation medium is intended for use in immobilised metal chelating affinity chromatography, the base matrix is commonly in beaded or monolithic form and made from natural polymers, e.g. agarose or dextran, or synthetic polymers, such as divinylbenzene or styrene. The base matrix can e.g. be in the form of a gel.

As regards natural polymers, suitable porous polymer beads thereof are either easily performed by the skilled person in this field according to standard methods, such as inverse suspension gelation (S Hjertén: Biochim Biophys Acta 79(2), 393-398 (1964) or spinning disk technique (see e.g. WO 88/07414 (Prometic Bio-Sciences Inc)). Alternatively, natural polymer beads are obtained from commercial sources, such as GE Healthcare Bio-Sciences AB, Uppsala, Sweden. Illustrative tradenames of such useful natural polymer beads are e.g. of the kind known as SEPHAROSE™ or SEPHADEX™.

In alternative embodiments, the base matrix can e.g. be a membrane, a filter, one or more chips, surfaces, capillaries etc.

In one embodiment, the reactive groups of the base matrix are allyl groups i.e. carbon-carbon double bonds. In one embodiment, a commercially available base matrix, which already exhibits allyl groups is used. In an alternative embodiment, the allyl groups are provided according to well known methods. Thus, in an illustrative embodiment, the present base matrix has been allylated by treatment with an epoxide carrying an allyl functionality at suitable temperatures and reaction times. One example of such a commonly used allyl-functional epoxide is allyl glycidyl ether (AGE). Accordingly, in a specific embodiment, in step (d), the sulphur group of the ligand is coupled to the base matrix via the activated allyl group of allyl glycidyl ether (AGE). In this embodiment, in the final product, the sulphur group will be attached to the base matrix by a spacer comprising ether groups and hydroxy groups, and the separation medium can be defined as base matrix —O—CH$_2$—CHOH—CH$_2$—O—CH$_2$—CHOH—CH$_2$—S— ligand.

In alternative embodiments, other well-known coupling techniques of thiol-containing ligands are used, such as opening of epoxide or radical addition to double bonds.

In a specific embodiment, said allyl groups are activated by bromination or alternatively, the coupling is a free radical reaction. The free radical used can be any suitable commercially available initiator, UV etc.

A second aspect of the present invention is a polydentate metal chelating affinity ligand or a separation medium comprising at least one, preferably a plurality of, polydentate metal chelating affinity ligands coupled to a base matrix, which medium has been generated by a method as described above. In a specific embodiment, the metal chelating affinity ligands are tridentate. Such a separation medium can then be charged with a suitable metal ion, such as Cu(II), Zn(II), Ni(II), Ca(II), Co(II), Mg(II), Fe(III), Al(III), Ga(III), Sc(II) etc, and used according to well known principles of IMAC, e.g. as outlined in the section "Background" above. In the most preferred embodiment, Ni$^{2+}$ is used.

In an advantageous embodiment, the present polydentate metal chelating affinity ligands are tridentate ligands which are defined by the formula

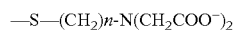
—S—(CH$_2$)$n$-N(CH$_2$COO$^-$)$_2$ wherein n is an integer of 1-6.

In a specific embodiment, the present separation medium, which comprises polydentate metal chelating affinity ligands coupled to a base matrix, is defined by the general formula

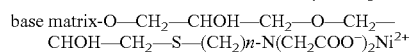
base matrix-O—CH$_2$—CHOH—CH$_2$—O—CH$_2$—
CHOH—CH$_2$—S—(CH$_2$)$n$-N(CH$_2$COO$^-$)$_2$Ni$^{2+}$ wherein n is an integer of 1-6. In one embodiment, n=2. In this context, it is understood that if the base matrix is e.g. in the form of a particle, then a plurality of ligands will be coupled to each particle as described above.

A third aspect of the invention is the use of cystamine as a starting material in the preparation of polydentate metal chelating ligands. The invention also encompasses the use of a carboxymethylated scaffold such as cystamine in the preparation of polydentate metal chelating ligands. In the most advantageous embodiment, said use is as defined above. As specified above, cystamine is commercially available from a number of sources (e.g. Sigma-Alrich, Acros, Fluka, Lancaster, Merck and Avocado).

In a fourth aspect of the invention, there is provided a ligand or medium which has been generated by the aforementioned method. Advantageously the ligand is a tridentate ligand.

A further aspect of the present invention is a kit, which comprises a scaffold as defined by the general formula (I) above, which kit comprises said scaffold in a solid state together with instructions, preferably written, for use thereof in the manufacture of metal chelating affinity ligands or a separation medium comprising polydentate metal chelating affinity ligands coupled to a base matrix. In an alternative embodiment, a kit according to the invention comprises any other form of the scaffold, such as a partly or fully derivatised scaffold, together with liquids and/or reagents suitable for performing the method according to the invention. In a specific embodiment, a kit is comprised of a scaffold reacted according to the present method except the deprotection, in which case the kit also comprises a suitable reagent for deprotection, such as a base or an acid, together with instructions for use.

The present invention also encompasses a chromatography column packed with a medium according to the invention. The column can be of any size, such as for large-scale production or lab-scale, or suitable for analytical purpose. The column can also be combined with separation medium and optionally liquids into a second kind of kit, which is also encompassed by the present invention. In one embodiment, the kit according to the invention comprises metal ions, such as Ni$^{2+}$ ions.

In addition, the present invention also relates to a process for separating a target substance from a liquid, which process comprises to provide a separation medium as defined above, to charge said medium with suitable metal ions to form chelates and to contact said medium with the liquid to adsorb the target substance thereon. In an advantageous embodiment, the process also comprises a step of eluting the target substance from the separation medium by adding a liquid that desorbs the target compound from the separation medium. In one embodiment, the elution is obtained by using a liquid that comprises a decreasing pH gradient or by applying a gradient giving an increasing imidazole concentration. The general principles of chromatography for separating a target substance as discussed above are well-known in this field, and the skilled person in this field can easily adopt the necessary parameters for use of the present process.

Finally, the present invention relates to a procedure of generating one or more diverse libraries of metal chelating affinity ligands for screening and optimising purposes. Thus, in this procedure, one arm carrying a dentate can be kept constant while other arms are selected in terms of optimal performance. As the skilled person will understand, for example one or more of the above-discussed $L_1$ and $L_2$ groups can be varied in order to identify the optimal form, and subsequently, once the optimised form has been identified, it is kept constant while other(s) are varied. Accordingly, the procedure of optimisation provides a tool to manufacture a separation medium comprising optimal, selected ligands.

DETAILED DESCRIPTION OF THE DRAWINGS

FIG. 1 provides a schematic illustration of the general route to produce a separation medium that comprises polydentate metal chelating affinity chromatography ligands according to the invention. FIG. 1 (a) illustrates the synthesis of the ligand in solution. The first step in FIG. 1 (a) corresponds to step (b) of the present method, i.e. a derivatisation, the second step is a reduction of the disulfide linkage (step (c) and the last step is deprotection of the functionalities of the ligand arms (i.e. step d). FIG. 1 (b) shows the immobilisation of the ligand to a gel, i.e. coupling of the ligand so produced to a base matrix. In FIG. 1, R denotes either hydrogen or alternatively an acid or base labile protecting group, and $X_1$ and $X_2$ can independently be selected from the group consisting of carbon, oxygen, sulphur and silicon.

Figure 2B:
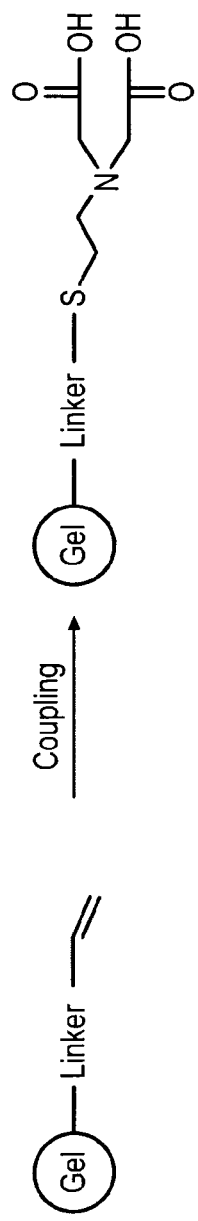

FIGS. 2 (a) and (b) is a schematic synthetic route to the production of a separation medium according to the invention, using cystamine as a scaffold. In FIG. 2 (a) cystamine is first derivatised, then reduced and finally deprotected, corresponding to steps (b), (c) and (d) of the present invention, to produce a polydentate ligand. The ligand is then coupled to a gel or base matrix, as shown in FIG. 2 (b), in readiness activation with metal ions.

Figure 3A:
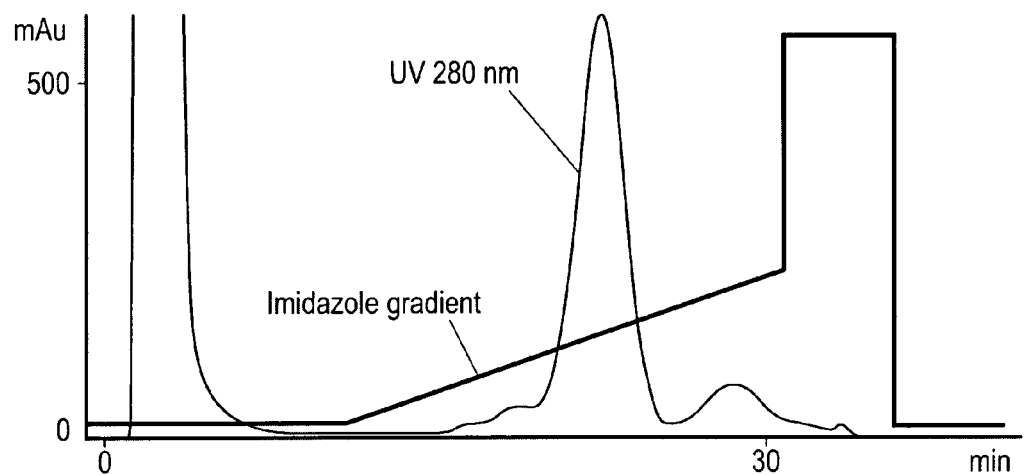
FIG. 3 (*a*) illustrates the purification of a Maltose Binding Protein from an *E. coli* extract with $(His)_6$-tail (MBP-His) using IMAC separation media prepared according to the invention.
Figure 3B:
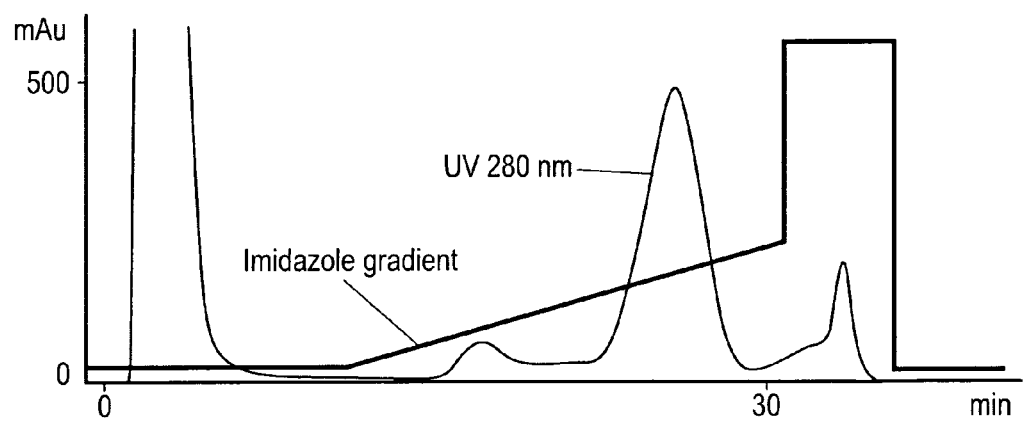

FIG. 3 depicts chromatograms obtained for the separation of a hexa histidine-tagged Maltose Binding Protein (MBP-His) from a lysate of *E. coli* using either
  a) a separation medium comprising polydentate ligands produced in accordance with the invention (FIG. 3 (a)); or
  b) a separation medium comprising Ni SEPHAROSE™ HP, which is a polydentate metal chelating affinity ligand which is commercially available from GE Healthcare Bio-Sciences AB, Uppsala, Sweden and described in WO 2004/076475.

The elution profiles of protein, as determined at A 280 nm, are shown against time and in response to increasing concentrations of imidazole.

Figure 4:
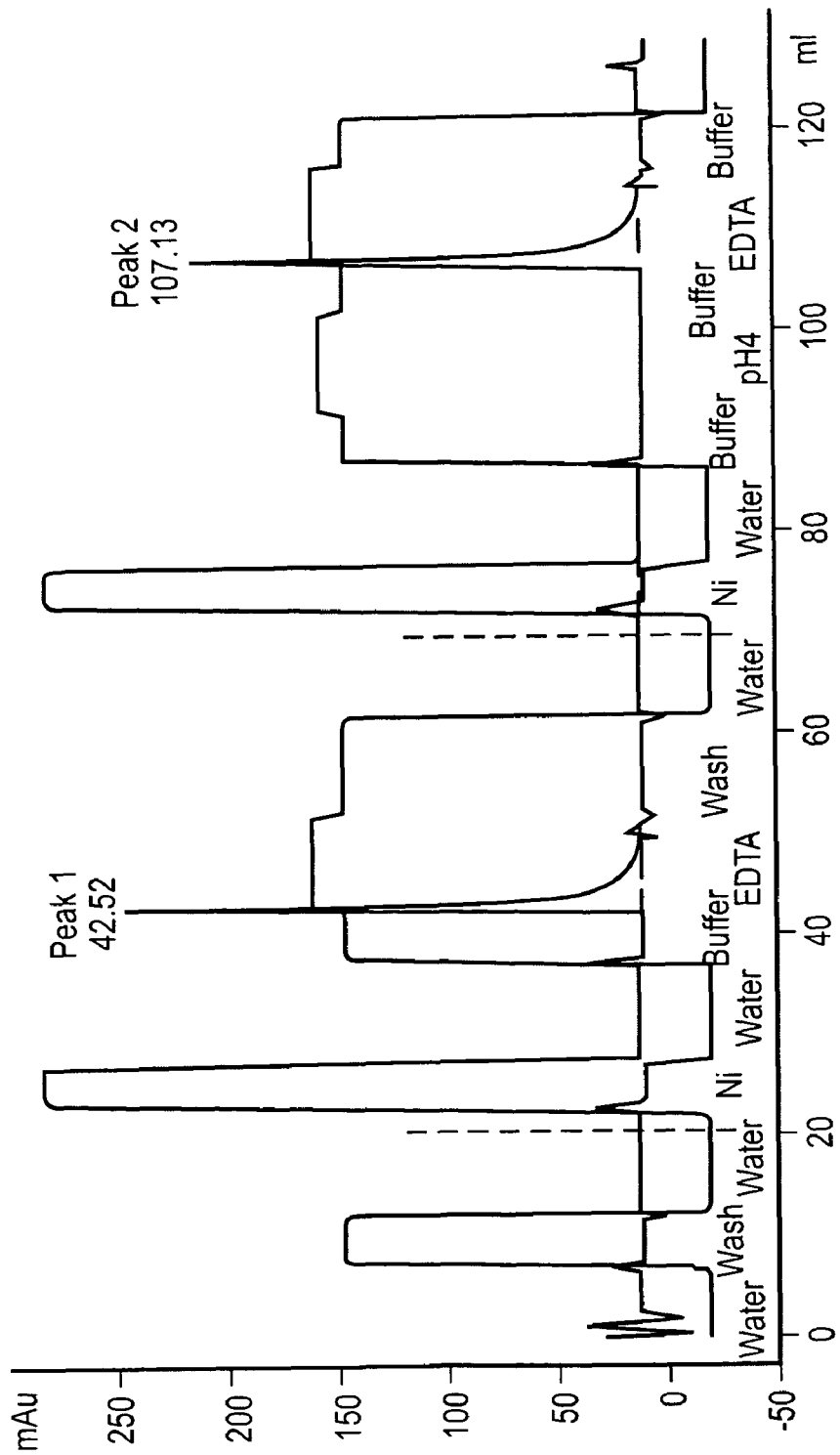
FIG. 4 shows a test chromatogram of the nickel binding capacity and nickel leakage at pH 4 of a separation medium prepared according to the present invention and tested as described in the experimental section below.

FIG. 4 is a test chromatogram showing the nickel binding capacity of a separation medium comprising a cystamine based ligand prepared according to the invention. The nickel binding capacity of the medium was determined by first charging the column with $Ni^{2+}$ ions, removing excess metal ions by washing with water and buffer, then elution of the nickel ions with EDTA (Peak 1). After recharging the column with $Ni^{2+}$ ions, the leakage of metal ions was tested in a similar manner; however, the gel was washed with an acetate buffer at pH 4.0 before elution with EDTA buffer (Peak 2). The leakage was expressed as a percentage of the binding capacity and was determined as the difference between the nickel-binding capacity and the amount eluted after washing at pH 4.0, according to the formula (area Peak 1−area Peak 2)/area Peak 1).

EXAMPLES

Below the present invention will be disclosed by way of examples, which are intended solely for illustrative purposes and should not be construed as limiting the present invention as defined in the appended claims. All references mentioned below or elsewhere in the present application are hereby included by reference.
1. Introduction to Experimental Studies and Results
1.1 General Analytical Methods
$^1$H-NMR and $^{13}$C-NMR NMR spectra were recorded on a Bruker 300 MHz using TMS as reference. LC-MS data were recorded using a Hewlett Packard 1100 MSD electro spray instrument.
1.2 Preparation and Coupling of Ligand to Base Media
1.2.1 Preparation of N,N'-Bis(di ethoxycarbonylmethyl) cystamine Cystamine dihydro chloride (homodimer) (5 mmol, 1.12 g, Sigma-Aldrich C12, 150-9) was dissolved in 100 ml of DMF and bromo acetic acid ethyl ester (30 mmol, 3.4 ml), potassium iodide (5 mmol, 0.83 g), and sodium hydrogen carbonate were added (25 mmol, 2.1 grams). The mixture was stirred over night at room temperature and the solvent was removed in vacu. The residue was partitioned between ethyl acetate and water. The organic phase was collected, dried over magnesium sulfate and concentrated in vacu. The remaining material was purified by flash chromatography on a silica column that was eluted with 1:1 mixture of pentane and ethyl acetate. The appropriate fractions were collected and concentrated in vacu yielding 1.1 g. The material was characterized with mass spectroscopy: ($Mw_{Calc.}$=496) 519.2 (M+Na), 497.3 (M+H), 212.2.
1.2.2 Preparation of Di Ethoxycarbonylmethyl Cystamine 0.24 grams of the above material was dissolved in 3 mL of water and Tris(carboxyethyl) phosphine (Sigma-Aldrich catalogue No C4706, CAS 51805-45-9) was added. The pH was adjusted to 12 with 0.5 M sodium hydroxide and the solution was stirred at room temperature for 2 hours. Analysis with LC-MS indicated that all starting material had been consumed.
1.2.3 Preparation of Di Carbonylmethyl Cystamine The aqueous solution from 1.2.2 above was extracted with ethyl acetate. The organic phase was collected and concentrated in vacu. The remaining material was dissolved in 1 M sodium hydroxide and the solution was stirred for 1.5 hours at room temperature. The material was characterized with mass spectroscopy: ($Mw_{Calc.}$=193) 216.1 (M+Na), 194.1 (M+H), 134.1
1.2.4 Allyl Activation of Base Matrix with Allyl Glycidyl Ether (AGE)

530 ml drained SEPHAROSE™ HP (GE Healthcare Biosciences, Uppsala, Sweden) was slurried with 135 ml distilled water in a round-bottomed flask equipped with a mechanical stirrer. To this, 6 g sodium hydroxide and 0.5 g NaBH$_4$ were added together with 60 g Na$_2$SO$_4$. The slurry was stirred at 50° C. for 30 minutes. Allyl glycidyl ether (75 g) was added to the reaction mixture and stirring continued at 50° C. for 18 h. The gel was then filtered on a glass filter and washed thoroughly with distilled water, ethanol, distilled water, 0.2 M HOAc, and distilled water.

The allyl content was measured with a titration method and determined as 35 μmol/ml gel. 2 ml drained SEPHAROSE™ HP (GE Healthcare Bio-Sciences, Uppsala, Sweden—35 μmol allyl/ml gel, batch No. 293610), which had been allyl activated as described above, was suspended with 3 ml distilled water in a round bottomed flask equipped with a mechanical stirrer. Sodium acetate (0.6 g) was added to the slurry and the mixture was stirred at room temperature for 5 min. Bromine water was added to the mixture until a permanent yellow colour was obtained and then stirred for a further 5 minutes. The excess bromine was removed with sodium-formate. The gel was then filtered on a glass filter and washed thoroughly with water.

1.2.5 Ligand Coupling to Base Matrix

Ligand solution was prepared by dissolving all material from the above preparation of di ethoxycarbonylmethyl cystamine in 2 ml of 1.0 M NaOH. The solution was stirred at room temperature for 145 minutes, thereafter 1.5 ml of 1.0 M NaHCO$_3$ was added together with 2.5 ml water. The pH was adjusted to 11.5 by adding 2 M NaOH. The solution was used immediately in the next step. The allyl brominated gel from 1.2.3 above was transferred into a round-bottomed flask equipped with a mechanical stirrer and to this the ligand solution was added. The reaction was kept at 43° C. overnight for 17 hours, and thereafter the gel was filtered and washed with ethanol, water and 20% ethanol.

1.3 Chromatographic Separation Using IMAC Separation Media

The following test was performed in order to characterise the selectivity and capacity of the IMAC separation media prepared according to the invention with known IMAC separation media. The test involves gradient purification of a hexa histidine-tagged Maltose Binding Protein (MBP-His) in an *E. coli* extract.

1.3.1 *E. Coli* Extract Containing MBP-His

The theoretical molecular mass (Mr) and Isolectric point (pI) of C-terminally hexaHis-tailed MBP-His is 43,781 and 5.4, respectively. The *E. coli* clone expressing MBP-His was a gift from Pharmacia Diagnostics.

Fermentation of recombinant *E. coli* BL21 [DE3] cells was performed in a fed-batch mode using complex culture medium complemented with 100 μg/ml carbenicillin and 25 μg/ml chloramphenicol antibiotics. Glucose solution was fed to the culture as carbone source during the process. Expression of the target protein was induced by addition of IPTG to a final concentration of 0.8 mM and the cultivation was finished 4 h post-induction. The cells were homogenised using approximately 1 g cell paste to 3 ml extraction buffer (the extraction buffer was 50 mM sodium phosphate pH 8,150 mM NaCl).

Stock solutions of 5 M NaCl and 2 M imidazole were added to the homogenised sample to final concentrations 0.5 M NaCl and 5 mM imidazole respectively. PMSF was added to a final concentration of 1 mM. The sample was centrifuged at 18000 rpm for 20 minutes and the supernatant was collected and frozen at −70° C. in portions until use. The concentration of MBP-His in this extract was estimated to be approximately 6.24 mg/ml.

1.3.2 IMAC A-Buffer

For one litre: one PBS tablet to 1000 ml water is specified to give 10 mM Na-phosphate, 140 mM NaCl and 3 mM KCl, pH 7.4. Two PBS tablets were dissolved in water, NaCl was added from 5 M stock to give an extra 220 mM (thus finally 140+140+220 mM=500 mM NaCl), the pH adjusted to 7.4 with sodium hydroxide and final volume diluted to 1000 ml. The buffer also contains 6 mM KCl.

1.3.3 Elution Buffer (IMAC B-Buffer)

This buffer was prepared in the same way as the IMAC A-buffer above, but imidazole was also added to 500 mM (from 2.0 M stock of imidazole-HCl, pH 7.4) before final adjustment of pH and volume.

1.3.4 Ni$^{2+}$-Sulphate Solution

A 100 mM nickel sulphate solution was prepared in water. The solution was filtered using a 0.2 μm membrane and the pH adjusted to 4.6.

1.3.5 Chromatography

Ligand coupled media (based upon cystamine as described in 1.2.5 above) and Ni SEPHAROSE™ HP (available from GE Healthcare Bio-Sciences, Uppsala, Sweden) were packed in separate HR5/5 columns (GE Healthcare Bio-Sciences, Uppsala, Sweden) to a bed height of 5 cm=1.0 ml bed. The media were charged with Ni$^{2+}$ prior to use by pumping the nickel sulphate solution onto the columns (5 column volumes), followed by water and by equilibration with binding buffer (=IMAC A-buffer with 5 mM imidazole added). A short blank run was performed by applying elution buffer, again followed by equilibration with binding buffer.

The *E. coli* extract with MBP-His, 0.5 M NaCl, 5 mM imidazole and 1 mM PMSF (freshly added) was clarified by centrifugation and frozen to −70° C. in portions (to get identical samples for the test). The required volume was then thawed and introduced into a 1 ml capillary LOOP™ (GE Healthcare Bio-Sciences, Uppsala, Sweden) through a 0.2 μm filter shortly prior to IMAC start. 0.75 ml was applied to a nickel-loaded and equilibrated column packed with a 1-ml bed of SEPHAROSE™ HP (GE Healthcare Bio-Sciences, Uppsala, Sweden) with ligand as described above. After extensive washing with binding buffer, a 20 ml linear gradient was run (to 40% Elution buffer=200 mM imidazole) using a chromatography system with a 2 mm UV-cell (ÄKTA™ Explorer 100 system, GE Healthcare Bio-Sciences, Uppsala, Sweden). Finally, a 5-ml push with 100% Elution buffer (500 mM imidazole) was applied. The flow rate was maintained at 1.0 ml/min throughout the experiments and absorbance was measured at 280 nm.

The absorbance curves obtained for the different IMAC media were used for comparison of selectivity (i.e. chromatographic pattern and resolution between the peaks) and capacity, as indicated by the elution position of the main peak containing MBP-His.

The resulting chromatograms (FIGS. 3 (*a*) and 3 (*b*)) highlight the excellent selectivity obtained with both the IMAC media to which di ethoxycarbonylmethyl cystamine had been coupled as described above (FIG. 3 (*a*)) and the Ni SEPHAROSE™ HP standard IMAC media (FIG. 3 (*b*)). As can be seen from the pattern of elution, the resolution between the peaks and the capacity of the media (as indicated by the elution position of the main peak corresponding to MBP-His), comparable levels of selectivity were observed with both the Ni SEPHAROSE™ HP standard media and media prepared according to the invention.

1.4 Determination of Metal-binding Capacity and Metal-leakage 1.4.1 Nickel-binding Capacity The nickel ($Ni^{2+}$) binding capacity of a separation medium prepared as described in 1.2.5 above for the cystamine based ligand was determined chromatographically using an ÄKTA™ Explorer 10 system (GE Healthcare Bio-Sciences, Uppsala, Sweden) equipped with a UV/Vis is detector. The test was performed on the gel, to which the cystamine based ligand had been coupled (see 1.2.5 above) and which had been packed in 1 ml HR5/5 columns (GE Healthcare Bio-Sciences, Uppsala, Sweden).

More specifically, a $NiSO_4$ solution (prepared as in 1.3.4 above but without any pH adjustment) was injected to load the gel with $Ni^{2+}$ ions. Excess metal was removed by washing with water and phosphate buffer (20 mM $PO_4$, 500 mM NaCl, pH 7.4). The nickel ions bound to the gel were eluted with EDTA, which is a very strong chelator and efficiently strips the metal ions from the gel. The peak area of the green coloured Ni-EDTA complex eluted was measured at 372 nm. A linear calibration curve was established from solutions with different concentrations of Ni-EDTA and was used for quantification. The nickel-binding capacity (FIG. 4, peak 1) was given as μmol Ni/ml packed gel.

The binding capacity of the separation medium was determined as 17 μmol/ml.

1.4.2 Metal Leakage

A metal leakage test was performed to test the stability of the ligand-nickel complex. The nickel-loaded gel was then washed with acetate buffer, pH 4.0. before determining the Ni content on the gel (FIG. 4).

Leakage of nickel ions was tested analogously to the above described nickel-binding capacity. However, before eluting nickel ions with EDTA, the gel was washed with ten column volumes of acetate buffer, 100 mM, pH 4.0. The leakage was given as % of the binding capacity and was determined as the difference between the nickel-binding capacity and the amount eluted after washing with pH 4, according to the formula: (area Peak 1-area Peak 2)/area Peak 1).

Metal leakage for the cystamine based ligand was determined to be 10% of the nickel binding capacity 1.7 μmol/ml.

The nickel binding capacity and metal leakage at pH 4 of the cystamine based ligand (which had been coupled to an allyl activated base matrix as described in 1.2.5 above) was compared to that of three prior art IMAC ligands—'Chelating SEPHAROSE™ HP', 'Ni SEPHAROSE™ HP' and 'NTA'. Chelating SEPHAROSE™ HP and Ni SEPHAROSE™ HP are available from GE Healthcare Bio-Sciences, Uppsala, Sweden, while NTA is commercially available from Qiagen Inc., Valencia, Calif., USA as the 'Ni-NTA' product range (e.g. Ni-NTA Superflow, Ni-NTA agarose). The nickel binding capacity and metal leakage tests were conducted as described above. Table 1 below shows the results of the comparative tests.

TABLE 1

Comparison of Ligand Metal Capacity and Leakage

| Ligand | Metal Capacity (μmol/ml) | Metal Leakage (at pH 4) |
|---|---|---|
| Cystamine based ligand | 17 | 10% |
| Chelating SEPHAROSE ™ HP | 21 | 19% |
| Ni SEPHAROSE ™ HP | 15 | 5% |
| NTA (Qiagen) | 16 | 9% |

As can be seen from Table 1, the metal leakage from the cystamine based ligand is significantly lower than from the related Chelating product. Furthermore, the metal binding capacity of the cystamine based ligand is comparable to that of Ni SEPHAROSE™ HP and NTA.

The present invention is useful for separating and purifying natural and synthetic substances which may be present in a solution. It is particularly useful for the separation of proteins, especially proteins which contain epitope tags. It is of particular use in the separation and/or purification of histidine tagged proteins.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for generating at least one polydentate metal chelating affinity ligand, said method comprising the steps of:
    (a) providing at least one scaffold defined by the general formula (I)

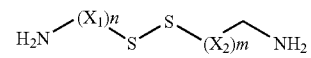

wherein $X_1$ and $X_2$ irrespective of each other are carbon atoms or heteroatoms, and n and m irrespective of each other are integers of 1 to 5;
    (b) providing at least one polydentate metal chelating affinity ligand arm, optionally in a form wherein the metal chelating functionalities of at least one said ligand arm are protected, on each said scaffold by derivatisation of the nucleophilic $NH_2$ groups of the scaffold;
    (c) reducing the disulfide bond of the derivatised scaffold; and, if required
    (d) deprotecting the functionalities of the ligand arm(s) provided in step (b).

2. The method of claim 1, wherein $X_1$ and $X_2$ are carbon atoms.

3. The method of claim 1, wherein $X_1$ and $X_2$ are carbon atoms, n=2 and m=1, and the scaffold is cystamine.

4. The method of claim 1, wherein in step (b) the derivatisation is provided by adding at least one derivatisation agent comprised of one part, which is electrophilic and hence capable of reacting with either or both of the $NH_2$ groups in Formula (I), and one part which is a metal chelating affinity ligand.

5. The method of claim 4, wherein the derivatisation is provided by adding two derivatisation agents, which comprise two different or identical metal chelating functionalities.

6. The method of claim 4, wherein one derivatisation agent is an halogenated, protected ester.

7. The method of claim 6, wherein one derivatisation agent is bromo-acetic acid ethyl ester.

8. The method of claim 1, wherein the metal chelating functionalities are protected in step (b), and subsequently wherein step (c) and step (d) are performed essentially simultaneously.

9. The method of claim 1, wherein steps (a) and (b) have been performed earlier to provide a ready-derivatised scaffold.

10. The method of claim 1, wherein the product obtained from step (d) is coupled via its thiol group to a base matrix to produce a separation medium.

11. The method of claim 10, wherein the thiol group is coupled to an epoxide group of the base matrix.

12. The method of claim 10, wherein the thiol group is coupled to an allyl group of the base matrix.

13. The method of claim 10, further comprising a step of allylation of a base matrix to provide reactive groups.

14. The method of claim 10, wherein the thiol group of the ligand is coupled to the base matrix via the allyl group of allyl glycidyl ether (AGE).

15. The method of claim 10, further comprising a step of activating the reactive groups of the base matrix.

16. The method of claim 15, wherein said activation is performed by bromination.

* * * * *